United States Patent
Weisshaupt et al.

(10) Patent No.: US 9,872,676 B2
(45) Date of Patent: Jan. 23, 2018

(54) SURGICAL RETRACTOR

(71) Applicant: Aesculap AG, Tuttlingen (DE)

(72) Inventors: Dieter Weisshaupt, Immendingen (DE); Pedro Morales, Tuttlingen-Nendingen (DE); Robert Vogtherr, Tuttlingen (DE); Andreas Elisch, Schramberg (DE); Peter Kleine, Neu Isenburg (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/851,468

(22) Filed: Sep. 11, 2015

(65) Prior Publication Data
US 2016/0000419 A1 Jan. 7, 2016

Related U.S. Application Data

(63) Continuation of application No. PCT/EP2014/052248, filed on Feb. 5, 2014.

(30) Foreign Application Priority Data

Mar. 21, 2013 (DE) .................. 10 2013 102 902

(51) Int. Cl.
*A61B 1/32* (2006.01)
*A61B 17/02* (2006.01)

(52) U.S. Cl.
CPC .. *A61B 17/0206* (2013.01); *A61B 2017/0237* (2013.01)

(58) Field of Classification Search
CPC .............. A61B 17/02; A61B 17/0293; A61B 2017/0237; B25B 5/082; B25B 5/125; B25B 7/14; B25B 13/14

(Continued)

(56) References Cited

U.S. PATENT DOCUMENTS

| 979,305 A | 12/1910 | Hunt | |
| 1,664,932 A * | 4/1928 | Juricinec | B25B 13/14 81/126 |

(Continued)

FOREIGN PATENT DOCUMENTS

| DE | 1 769 072 | 6/1958 |
| DE | 2 359 085 | 6/1974 |

(Continued)

OTHER PUBLICATIONS

Aurelio Chaux, M.D., and Carlos Blanche, M. D., "A New Concept in Sternal Retraction: Applications for Internal Mammary Artery Dissection and Valve Replacement Surgery". The Annals of Thoracic Surgery, vol. 42, No. 4, Oct. 1986, pp. 473-474.

(Continued)

*Primary Examiner* — Tatiana Nobrega
*Assistant Examiner* — Jessica Weiss
(74) *Attorney, Agent, or Firm* — Lipsitz & McAllister, LLC

(57) ABSTRACT

The invention relates to a surgical retractor, in particular, for spreading a severed sternum, comprising a first retaining device and a second retaining device, which each have a spreader arm with at least one retaining element held thereon, a holding device for holding the retaining devices on each other, and a drive device with which the distance of the spreader arms from each other along a retraction direction is alterable for transfer to a spread position. In order to provide a retractor of this kind which, having a compact design, is easy to handle, it is proposed in accordance with the invention that the retaining devices each have a holding arm connected to the respective spreader arm, and both holding arms couple with the drive device and be displaceable via the drive device relative to each other and relative to the holding device along a displacement direction.

19 Claims, 9 Drawing Sheets

(58) Field of Classification Search
USPC ............ 600/201–235; 269/143, 249, 67–69; 81/485, 165–166, 170–171
See application file for complete search history.

(56) References Cited

U.S. PATENT DOCUMENTS

| | | |
|---|---|---|
| 2,670,731 A | 3/1954 | Zoll et al. |
| 3,195,536 A | 7/1965 | Hovnanian et al. |
| 3,522,799 A | 8/1970 | Gauthier |
| 3,592,199 A | 7/1971 | Ostensen |
| 3,749,088 A | 7/1973 | Kohlmann |
| 3,796,214 A | 3/1974 | Davis |
| 3,986,854 A | 10/1976 | Scrivo et al. |
| 4,562,832 A | 1/1986 | Wilder et al. |
| 4,566,448 A | 1/1986 | Rohr, Jr. |
| 4,570,614 A | 2/1986 | Bauman |
| 4,597,030 A | 6/1986 | Brody et al. |
| 4,747,394 A * | 5/1988 | Watanabe .......... A61B 17/0206 600/217 |
| 4,805,599 A | 2/1989 | Ray |
| 4,867,139 A | 9/1989 | Girzadas |
| 4,932,395 A | 6/1990 | Mehdizadeh |
| 4,971,038 A | 11/1990 | Farley |
| 5,002,547 A | 3/1991 | Poggie et al. |
| 5,027,793 A | 7/1991 | Engelhardt et al. |
| 5,035,232 A | 7/1991 | Lutze et al. |
| 5,303,694 A | 4/1994 | Mikhail |
| 5,363,841 A | 11/1994 | Coker |
| 5,364,399 A | 11/1994 | Lowery et al. |
| 5,728,046 A | 3/1998 | Mayer et al. |
| 5,730,757 A | 3/1998 | Benetti et al. |
| 5,944,736 A | 8/1999 | Taylor et al. |
| 5,976,171 A | 11/1999 | Taylor |
| 6,113,536 A | 9/2000 | Aboul-Hosn et al. |
| 6,478,734 B1 | 11/2002 | Taylor et al. |
| 6,602,189 B1 | 8/2003 | Bennetti et al. |
| 7,288,065 B1 | 10/2007 | Taylor et al. |
| 7,699,774 B1 | 4/2010 | Taylor et al. |
| 7,909,846 B1 | 3/2011 | Taylor et al. |
| 8,092,495 B2 | 1/2012 | Boulis et al. |
| 8,715,175 B2 | 5/2014 | Assaker et al. |
| 2003/0060686 A1 | 3/2003 | Taylor et al. |
| 2007/0161865 A1 | 7/2007 | Fakhrai |
| 2008/0139879 A1 | 6/2008 | Olson et al. |
| 2008/0183046 A1 * | 7/2008 | Boucher ............ A61B 17/0206 600/232 |
| 2008/0188718 A1 * | 8/2008 | Spitler ............... A61B 17/0206 600/213 |
| 2009/0203969 A1 | 8/2009 | Cohen et al. |
| 2009/0259107 A1 | 10/2009 | Crenshaw et al. |
| 2010/0030184 A1 * | 2/2010 | Boulis ................ A61B 17/0206 604/500 |
| 2010/0185059 A1 * | 7/2010 | Sperling ................ A61B 17/02 600/219 |
| 2012/0022335 A1 | 1/2012 | Assaker et al. |
| 2013/0046147 A1 | 2/2013 | Nichter et al. |
| 2015/0018624 A1 | 1/2015 | Beck et al. |

FOREIGN PATENT DOCUMENTS

| | | |
|---|---|---|
| DE | 30 23 266 | 1/1982 |
| DE | 33 01 890 | 7/1984 |
| DE | 297 23 643 | 1/1999 |
| DE | 20 2011 051 999 | 1/2012 |
| DE | 20 2012 100 124 | 4/2012 |
| EP | 0 101 781 | 3/1984 |
| EP | 0 327 249 | 8/1989 |
| EP | 0 856 286 | 8/1998 |
| EP | 2 394 584 | 12/2011 |
| FR | 2657246 | 7/1991 |
| FR | 2 692 468 | 12/1993 |
| FR | 2 742 330 | 6/1997 |
| JP | S12-4341 | 4/1937 |
| WO | WO 01/80725 | 11/2001 |
| WO | WO 2009/124244 | 10/2009 |

OTHER PUBLICATIONS

"Fiberoptics for Surgery", Applied Fiberoptics, Inc., cover page, pp. 5, 6, and two product information sheets, undated. (retyped p. 6 attached for clarity).

Spiggle & Theis Medizintechnik GMBH, "Oral Cavity Instruments", catalog, 2012, 76 pages.

* cited by examiner

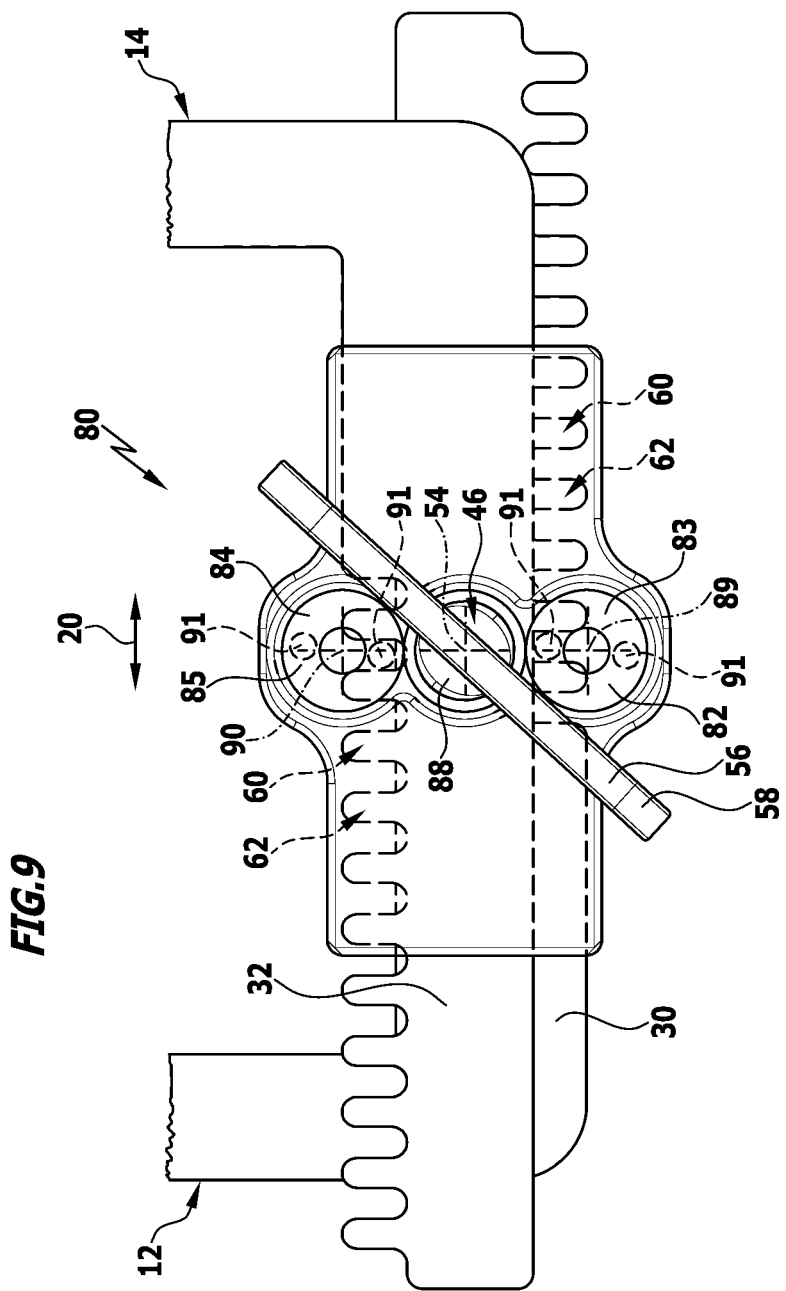

# SURGICAL RETRACTOR

CROSS-REFERENCE TO RELATED APPLICATIONS

This application is a continuation of international application number PCT/EP2014/052248 filed on Feb. 5, 2014 and claims the benefit of German application No. 10 2013 102 902.7 filed on Mar. 21, 2013, which are incorporated herein by reference in their entirety and for all purposes.

FIELD OF THE INVENTION

The present invention relates to a surgical retractor, in particular, for spreading a severed sternum, comprising a first retaining device and a second retaining device, which each have a spreader arm with at least one retaining element held thereon, a holding device for holding the retaining devices on each other, and a drive device with which the distance of the spreader arms from each other along a retraction direction is alterable for transfer to a spread position.

BACKGROUND OF THE INVENTION

A retractor of the aforementioned kind is used, in particular, in operations on the thoracic cage in order to provide access to the heart. Herein the sternum is severed at the center in the longitudinal direction and a spreader arm with the respective at least one retaining element is positioned on each sternum side. By actuating the drive device, the spreader arms are transferred from an unspread position to a spread position along the retraction direction and the sternum held back by the retaining elements is spread open. The spreader arms usually define a spreading plane in which the spreading occurs.

In known retractors, one spreader arm is movable relative to the other spreader arm to which the holding device is rigidly secured. For this purpose, the movable spreader arm is usually connected to a holding arm which is held on the holding device. In order that the spreader arms, in the spread position, can be spaced far enough apart for the surgical intervention, it is necessary, in the known retractors, for the holding arm of the movable retaining device to project at the side to a not inconsiderable extent over the other retaining device. The operating surgeon may find this interfering. Such a holding arm can also prove disadvantageous, in particular, when one sternum half in the spread state is lifted out of the spreading plane and may thereby collide with the holding arm.

An object underlying the present invention is to provide a generic retractor which, having a compact design, is easy to handle.

SUMMARY OF THE INVENTION

In an aspect of the invention, a surgical retractor, in particular, for spreading a severed sternum, comprises a first retaining device and a second retaining device, which each have a spreader arm with at least one retaining element held thereon, a holding device for holding the retaining devices on each other, and a drive device with which the distance of the spreader arms from each other along a retraction direction is alterable for transfer to a spread position. The retaining devices each have a holding arm connected to the respective spreader arm, and both holding arms couple with the drive device and are displaceable via the drive device relative to each other and relative to the holding device along a displacement direction.

BRIEF DESCRIPTION OF THE DRAWINGS

The foregoing summary and the following description may be better understood in conjunction with the drawing figures, of which:

FIG. 9 shows a partial representation of the retractor from FIG. 7 in a plan view.

DETAILED DESCRIPTION

Figure 1:
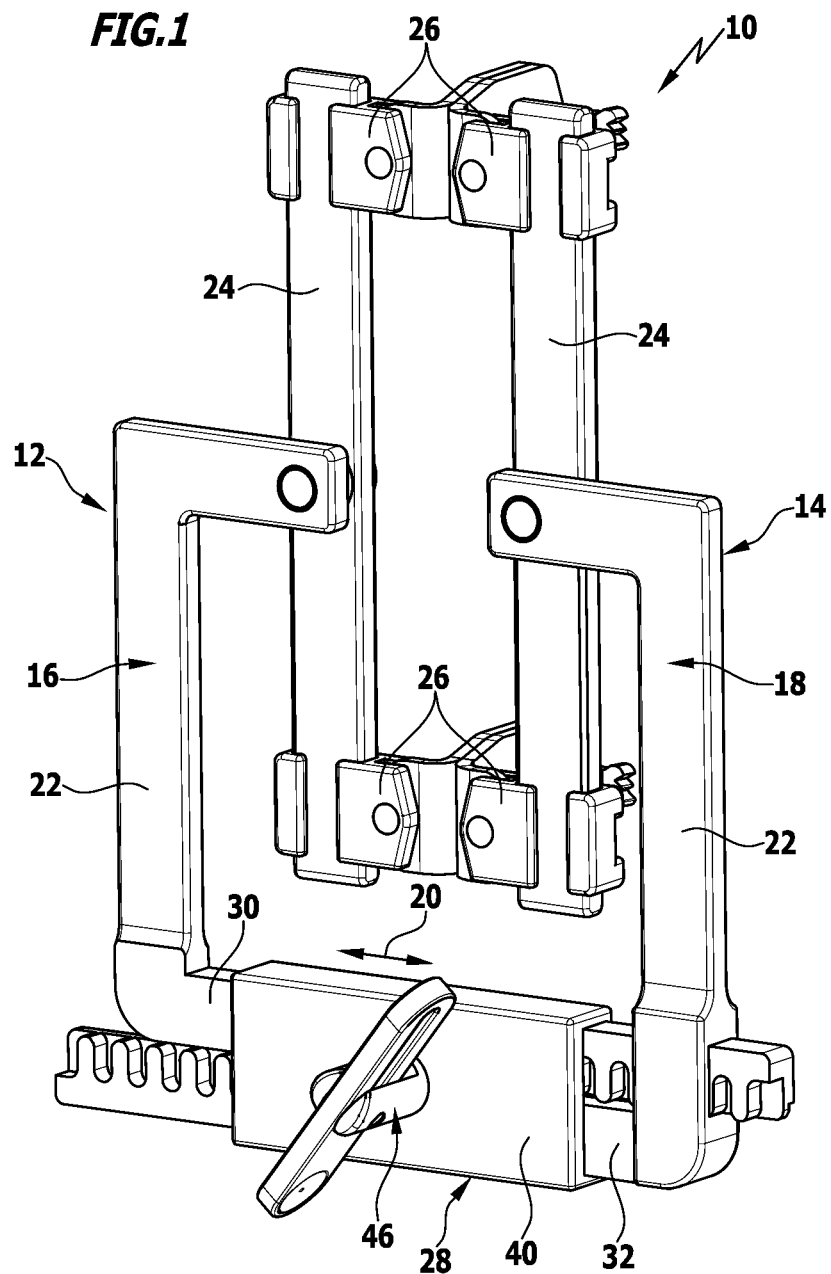
FIG. 1 shows a perspective representation of a first preferred embodiment of a retractor in accordance with the invention.
Figure 2:
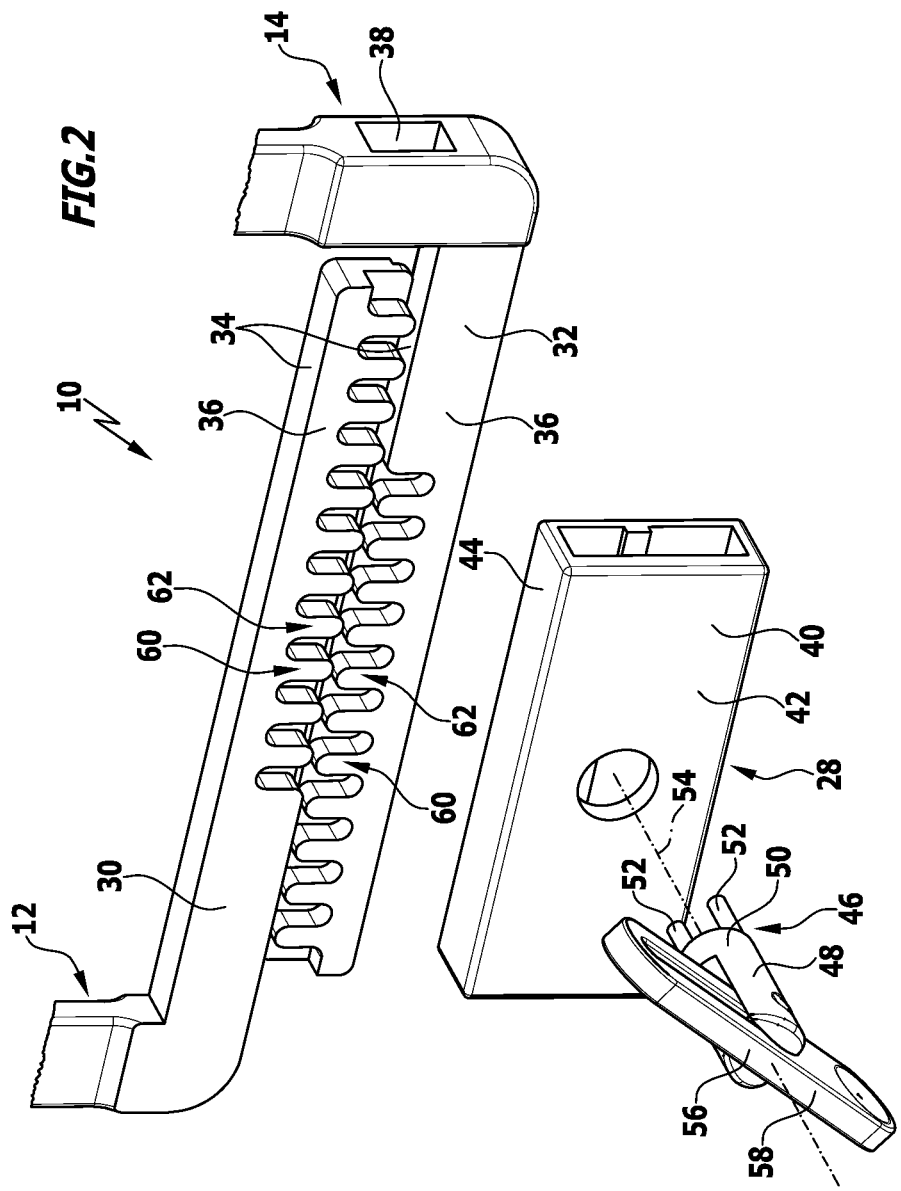
FIG. 2 shows a partial view of the retractor from FIG. 1 in an exploded representation.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical retractor, in particular, for spreading a severed sternum, comprising a first retaining device and a second retaining device, which each have a spreader arm with at least one retaining element held thereon, a holding device for holding the retaining devices on each other, and a drive device with which the distance of the spreader arms from each other along a retraction direction is alterable for transfer to a spread position. The retaining devices each have a holding arm connected to the respective spreader arm, and both holding arms couple with the drive device and are displaceable via the drive device relative to each other and relative to the holding device along a displacement direction.

In the retractor in accordance with the invention, both retaining devices have a holding arm, and the holding arms are displaceable relative to each other and relative to the holding device. By using only one drive device, the holding arms and, therefore, the retaining devices can be driven and displaced relative to each other along a displacement direction. A particularly compact design of the retractor can thereby be achieved, in particular, when the holding device and the drive device, in relation to the retraction direction, are arranged between the spreader arms. In particular, this makes it possible to displace the retaining devices in opposite directions for spreading in directions facing away from each other. Unlike in conventional retractors, each retaining device covers part of the distance relative to the holding device, which is necessary for transferring the spreader arms to the spread position. This is favorable for the more compact design of the retaining device. Moreover, practice shows that as a result of driving both holding arms, the drive device undergoes less wear than in generic retractors in which only one of the retaining devices is driven.

It is expedient for the displacement direction to be aligned parallel to the retraction direction. A constructionally simpler configuration can thereby be imparted to the retractor.

It is advantageous for the holding device and/or the drive device to be arranged, in relation to the retraction direction, in each case, at least partially, midway or substantially midway between the spreader arms, in order to achieve a compact design of the retractor. For example, the holding device and/or the drive device is/are arranged and centered around a center plane of the retractor, which center plane is aligned perpendicularly to a spreading plane defined by the spreader arms. Starting from the center plane, both retaining devices can move in opposite directions by being driven by the drive device and so a small overall width can be imparted to the retractor.

It is particularly advantageous for the holding device and/or the drive device, irrespective of the distance of the spreader arms from each other, to be arranged midway or substantially midway between the spreader arms. It is thereby made possible for the holding device and/or the drive device to remain stationary in relation to the patient's body, whereas the retaining devices can be transferred over the same displacement distance relative to the patient's body to the spread position.

The holding device and/or the drive device is/are preferably arranged in or substantially in a spreading plane defined by the spreader arms. A flat design can thereby be imparted to the retractor, which is found to be less interfering by the operating surgeon.

The holding arms are preferably displaceable over the same distance relative to the holding device upon actuation of the drive device. In particular, this makes it possible to displace the retaining devices symmetrically to each other in relation to the holding device. Irrespective of the distance of the spreader arms from each other, the holding device can be arranged midway between the retaining elements.

For a flat and compact design of the retractor, it is advantageous for the holding arms to be of rail-shaped configuration.

It is expedient for the holding device to comprise or form a housing which at least partially engages around the holding arms. The housing can thereby hold the holding arms together. At least one drive element of the drive device can be arranged in the housing, and drive elements or drive tracks arranged on the holding arms, which will be discussed hereinbelow, can be arranged at least partially in the housing. Direct access to the drive tracks and/or the drive element can thereby be at least partially prevented. This reduces, for example, the likelihood of surgical suture material getting caught on the drive element or the drive tracks and blocking these.

The housing advantageously engages around the holding arms completely or substantially completely. The housing can be expediently closed in itself in a plane transverse to the displacement direction.

It is advantageous for the housing to be configured as flat housing. The flat housing can have broad and narrow sides, and during designated use of the retractor a broad side preferably faces the patient's body. When the retractor is used to spread a sternum, the retractor can, for example, thereby be positioned better on the thoracic cage.

The holding arms can engage the housing from opposite sides and/or extend through the housing. When spreading the retaining devices relative to each other, free ends of the holding arms can be displaced in the direction towards the housing and a side of a holding arm connected to the respective spreader arm moved away from the housing. Conversely, when the spreader arms are made to approach each other, the respective side of a holding arm connected to a spreader arm can be displaced in the direction towards the housing and a free end of the holding arm moved away from the housing.

It is advantageous for the holding device to form a guide for at least one of the holding arms and preferably for both holding arms. A reliable functioning of the retractor can thereby be ensured.

Additionally or alternatively, in order to achieve the same advantage, it is expedient for the holding arms to lie against each other and, when displaced, to mutually guide each other relative to each other.

For example, it may be provided that the holding arms have broad sides and narrow sides, and that the holding arms lie via the respective broad sides with surface-to-surface contact against each other, it being possible for them to mutually guide each other.

The holding arms are preferably arranged in or substantially in the spreading plane. The retractor can thereby have a flat design.

The drive device is preferably arranged on the holding device or included in the holding device. For example, the drive device is at least partially integrated in the holding device. In particular, at least one drive element of the drive device is arranged in a housing of the holding device.

In a constructionally simple retractor, the reliable functioning of which can be ensured, it is expedient for the drive device to comprise at least one drive element, and for the holding arms to each comprise a drive track extending in the displacement direction, the at least one drive element interacting with the respective drive track. By acting on the at least one drive element, the respective drive track of a holding arm can be driven and the holding arm thereby displaced.

The at least one drive element can be arranged midway or substantially midway between the spreader arms, in relation to the retraction direction and preferably irrespective of the distance of the spreader arms from each other.

The at least one drive element and/or the drive tracks can undergo wear-reducing manufacturing or treatment processes and/or include low-wear materials or be produced from such materials. For example, surface and/or heat treatments such as, for example, nitriding, surface layer hardening, boriding, case hardening or the like can be performed on the at least one drive element and/or the drive tracks. It is also possible to produce a specified difference in hardness between the interacting at least one drive element and the drive tracks, in order to optimize the wear.

Furthermore, the wear can be reduced by the use of suitable materials, for example, by a wear-favorable combination of materials consisting of ceramic or plastic material, on the one hand, and metal, on the other hand.

Corresponding processes and/or corresponding materials can be used in all parts of the retractor that are movable relative to one another. For example, the holding arms, on the one hand, and a housing of the holding device, on the other hand, can be optimized with respect to a reduction in wear. It is also conceivable for the actuating element, mentioned again hereinbelow, of the drive device and, in particular, a housing of the holding device to be adapted to each other with respect to a reduction in wear.

The at least one drive element and the drive tracks can form a linear drive so that the holding arms can be driven in a constructionally simple way.

Expediently, the drive tracks are of identical configuration.

It proves advantageous for the drive track to be configured as row of teeth arranged on the respective holding arm, and for the at least one drive element to be configured as pin wheel or gear wheel which meshes with the row of teeth. This allows the holding arms to be driven via a toothing with the at least one drive element, for example, a lantern gear toothing.

In a different advantageous embodiment of the retractor in accordance with the invention, it may be provided that a roller track is used as drive track, and that the at least one drive element is configured as roller rolling on the roller track.

Expediently, the at least one drive element is mounted on the holding device for rotation about an axis of rotation perpendicular to the displacement direction. By rotating the drive element, in particular, a pin wheel or a gear wheel, the respective holding arm can thereby be driven.

It is advantageous for the drive device to comprise at least one hand-operated actuating element, preferably in the form of a crank or a rotary handle, for acting on the at least one drive element. By rotating the crank or the rotary handle, the at least one drive element can be rotated, in particular, about the aforementioned axis of rotation and preferably thereby meshes with the aforementioned row of teeth.

The actuating element is preferably removable. When the spreader arms adopt a desired spread position, the actuating element can be removed so as to allow the operating surgeon even better access to the surgical site. The at least one actuating element is preferably removable without a tool.

The retractor advantageously comprises a fixing device with which the retaining devices are fixable in a spread position, specifically after removal of the actuating element.

In an advantageous embodiment, it proves expedient for at least one holding arm to have an elongated hole aligned along the displacement direction, at the edge of which the drive track is arranged. The likelihood of foreign matter such as, for example, surgical suture material getting caught on the row of teeth is thereby reducible.

It may be provided that the drive tracks are arranged on sides of the holding arms that face away from each other. In such an embodiment, in particular, two drive elements may be provided, a respective one of which interacts with a drive track.

In practice, it proves advantageous for the holding arms to have broad sides and narrow sides, and for the drive tracks to be arranged on the narrow sides. In this case, it is possible for the drive tracks to be arranged on narrow sides that face each other or face away from each other.

The drive tracks can be arranged in a common plane or in parallel planes, preferably parallel to the spreading plane or in the spreading plane.

It proves expedient for the drive device to comprise a drive element which interacts with the drive tracks of both holding arms. For example, a drive element in the form of a pin wheel or gear wheel is provided, which simultaneously meshes with two drive tracks configured as rows of teeth. By a rotation of the drive element, the retaining elements can thereby be spaced at a distance from each other, which is twice the size of the displacement path of each holding arm.

In order to achieve a compact design, it may expediently be provided for the drive tracks of the holding arms to face each other, and for the drive element to engage a space between the drive tracks. The drive tracks are arranged, for example, on narrow sides of the holding arms, which face each other. It may also be provided that the holding arms lie against each other via broad sides and each comprise an elongated hole extending along the displacement direction, at the edge of which the drive tracks are arranged.

In a different advantageous embodiment of the retractor in accordance with the invention, it is expedient for the drive device to comprise two drive elements, each drive element interacting with a drive track of a holding arm. The drive elements couple with one drive track, in each case, and the drive tracks are arranged, for example, on sides of the holding arms that face away from each other.

It proves advantageous for the drive elements to be drivable together. The drive device preferably comprises a further drive element which is coupled to the actuating element and meshes with the two drive elements. In particular, this makes it possible to provide a gearing in the drive device. A drive element, which couples with the two drive elements interacting with the drive tracks can be driven by the actuating element. This makes it possible to provide a desired gearing-up or gearing-down between the coupling drive elements. This allows the rotational speed of the drive elements and, therefore, the adjusting range of the holdings arms to be set in a constructionally simple way so as to meet the individual requirements.

All in all, it is expedient for the drive device to comprise or form a gearing with which a rotational speed of the at least one drive element configured as rotary body, in particular, as gear wheel or pin wheel is alterable.

The gearing is preferably accommodated in a housing included in or formed by the holding device. Direct access to the gearing can thereby be advantageously prevented. The likelihood that foreign matter such as, for example, surgical suture material will be drawn into the gearing is thereby reduced.

It proves expedient for at least one of the holding arms to extend through a guide on the respective other retaining device. For example, a guide is provided at an edge of a through-opening on a spreader arm of a retaining device for a holding arm of the other retaining device.

To achieve a constructionally simple configuration, it may be provided that each holding arm is integrally connected to the respective spreader arm.

FIG. 1 shows in a perspective representation a first preferred embodiment, denoted in its entirety by reference numeral 10, of a surgical retractor in accordance with the invention. The retractor 10 is provided, in particular, for spreading a sternum, not shown in the drawings, in order, for example, to enable an operating surgeon to access the opened thoracic cage when performing a heart operation.

The retractor 10 comprises two retaining devices 12 and 14. The retaining devices 12, 14 comprise spreader arms 16 and 18, respectively, which can be spaced at a variable distance from each other by being displaced along a retraction direction 20 relative to each other in a manner explained hereinbelow. The retraction direction 20 is therefore also a displacement direction 20 of the retractor.

Details of the exact configuration of the spreader arms 16, 18 are not of importance for an understanding of the present invention. It is merely essential that the spreader arms 16, 18 comprise at least one retaining element each and be able to be spaced at a variable distance by displacement relative to each other. They can thereby be transferred to a spread position (not shown) along the retraction direction 20. The patent application DE 10 2012 100 284.3 of the same applicant, which is not a prior publication, includes a plurality of further configurations of spreader arms which, for example, in the retractor 10 can be used instead of the spreader arms 16, 18. In connection with such configurations, reference is made to the patent application DE 10 2012 100 284.3, the disclosure content of which is included in full in the present application.

Each spreader arm 16, 18 comprises a first section 22 which is of L-shaped configuration, with the angled part facing in the direction of the respective other spreader arm 18, 16. Each spreader arm 16, 18 further comprises a second section 24 which is mounted at the end of the first section 22 so as to be pivotable about an axis of rotation. The axis of rotation is aligned perpendicularly to a spreading plane which is defined by the spreader arms 16, 18 and in which the sternum is spread using the retractor 10. The second sections 24 are of straight-lined and elongated configuration and are mounted approximately at their center so as to be pivotable on the first sections 22. A retaining element 26 is held in the area of end sections on each second section 24. The retaining elements 26 each comprise an angled bracket which can be positioned on the sternum. The retaining elements 26 of the spreader arms 16, 18 are thereby positioned on both sternum halves in such a way that these can be spread upon movement of the spreader arms 16, 18. The retaining elements 26 can be held so as to be changeable in their position on the second sections 24, for example, mounted on these so as to be pivotable relative to the spreading plane or displaceable along the second sections 24.

The retractor 10 comprises a holding device 28 for holding the retaining devices 12, 14 on each other. For this purpose, the retaining devices 12, 14 comprise holding arms 30 and 32, respectively. Both holding arms 30, 32 are of straight-lined and elongated configuration in the form of rails having narrow sides 34 and broad sides 36. The holding arm 30 is connected at the spreader arm 16 preferably integrally to its first section 22, more specifically, at the end of the first section 22 located opposite the second section 24. The holding arm 30 is angled relative to the first section 22, preferably through 90°, and it faces in the direction of the spreader arm 18.

In a corresponding manner, the holding arm 32 is fixed preferably integrally to the first section 22 of the spreader arm 18. The holding arm 32 is angled relative to the first section 22, preferably through 90°, and it faces in the direction of the spreader arm 16. The connection to the first section 22 is made at its end located opposite the second section 24.

The first section 22 of the spreader arm 18 has a through-opening 38. The holding arm 30 can extend through the through-opening 38 without play or engage it and thereby be guided on the spreader arm 18. When the retractor 10 adopts an unspread position (FIG. 1), in which the retaining elements 26 of both spreader arms 16, 18 lie against each other, the holding arm 30 extends through the through-opening 38. Even when the retractor 10 is spread somewhat (not shown) the holding arm 30 can still be guided by the spreader arm 18.

The holding arms 30, 32 are aligned flush with each other in one plane and arranged such that narrow sides 34 face each other.

The holding device 28 comprises a housing 40 which is configured as flat housing. Accordingly, the housing 40 has two broad sides 42 and two narrow sides 44. The broad sides 42 and narrow sides 44 form a casing which engages around and, in particular, encloses both holding arms 30, 32. In other words, the housing 40 is closed in itself in the circumferential direction of the holding arms 30, 32. The holding arms 30, 32 engage the housing 40 from opposite sides and can extend through it. Depending on the extent to which the retractor 10 is spread and which spread position the spreader arms 16, 18 adopt, the holding arms 30, 32 still project with their free ends from the housing 40. If the retractor 10 is spread far, the free ends of the holding arms 30, 32 may also be located in the housing 40.

In addition to holding the retaining devices 12, 14, the housing 40 also serves to guide them when the holding arms 30, 32 are displaced relative to the housing 40 and relative to each other along the retraction direction 20.

Via one of the broad sides 42 facing the upper part of the patient's body when the retractor 10 is in use, the retractor 10 can lie with surface-to-surface contact on his thoracic cage.

Furthermore, a drive device 46 of the retractor 10 is arranged on the holding device 28. The drive device 46 comprises a drive element 48 which, in the present case, is configured as a pin wheel 50. The pin wheel 50 is of cylindrical configuration, and it comprises two pins 52 on an end face arranged in the housing 40. The pins 52 are diametrically opposed to each other in relation to an axis of rotation 54 defined by the pin wheel 50. The axis of rotation 54 is aligned perpendicularly to the spreading plane. At the end located opposite the pins 52, an actuating element 56 of the drive device 46 is held on the pin wheel 50. The actuating element 56 is hand-operated and, in the present case, is configured as crank 58. The pin wheel 50 and the crank 58 connected thereto are mounted on the housing 40 for rotation about the axis of rotation 54.

It may be provided that the crank 58 is removable from the pin wheel 50 or together with the latter from the housing 40 in order to enable an operating surgeon, when the retractor 10 is in use, to have even better access to the surgical site after the spreading of the sternum.

The drive device 46 further comprises two rows of teeth 60. The rows of teeth 60 are arranged on the holding arms 30, 32, more specifically, in each case, on the narrow side 34 facing the respective other holding arm 30, 32. Each row of teeth 60 comprises a plurality of teeth. In the present case, 11 teeth are provided. The teeth are formed by cut-outs formed on the narrow sides 34 of the holding arms 30, 32, with the remaining teeth cut out of these. The teeth are equidistantly spaced from one another, and they extend from the free ends of the holding arms 30, 32 over approximately 60% of their length.

The pin wheel 50 and the rows of teeth 60 form lantern gear toothings which are configured as linear drives.

Figure 3:
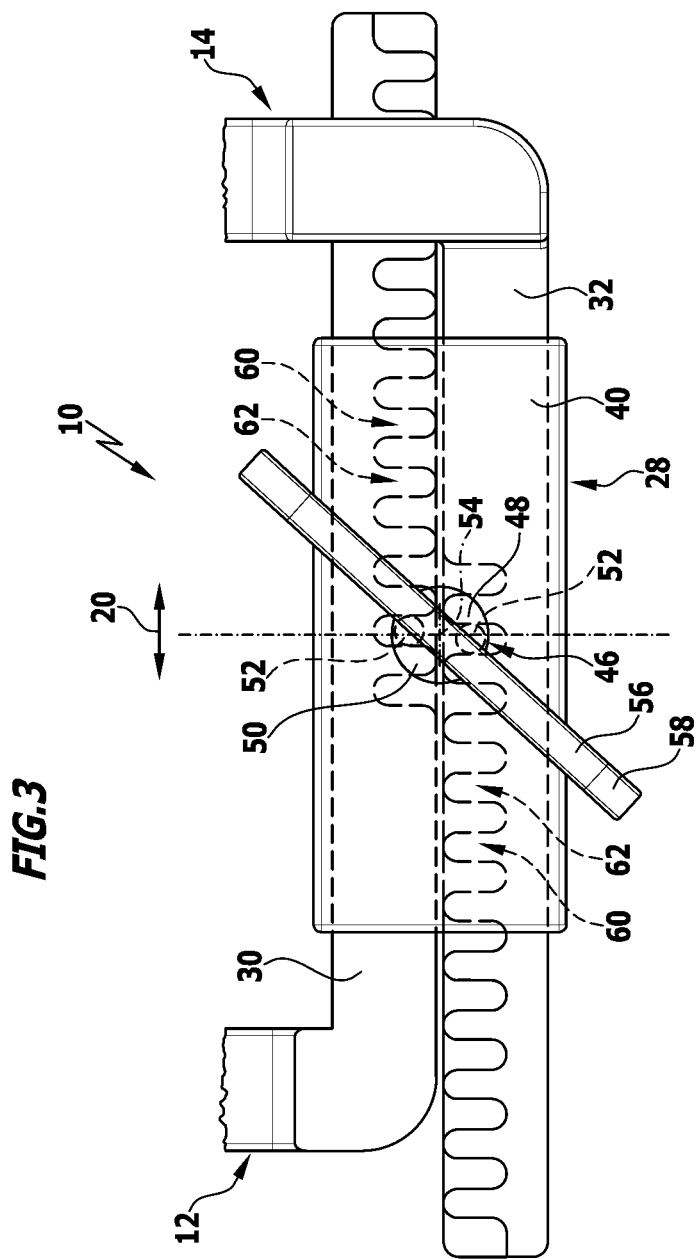
FIG. 3 shows a partial representation of the retractor from FIG. 1 in a plan view.

Both rows of teeth 60 can couple simultaneously with the pin wheel 50 and so both retaining devices 12, 14 can be driven and displaced relative to each other using only one crank 58. As is clear, in particular, from FIG. 3, pins 52 engage the spaces between the teeth of both rows of teeth 60. By rotating the crank 58 and, therefore, the pin wheel 50 about the axis of rotation 54, the pins 52 can enter into alternating engagement with the teeth on the holding arms 30 and 32 and thereby displace both holding arms 30, 32 along the retraction direction 20 relative to each other. As both holding arms 30, 32 can be driven, the rows of teeth 60 are also referred to as drive tracks 62 of the drive device 46.

Upon rotating the crank 58, both holding arms 30, 32 are displaced in opposite directions relative to each other and relative to the housing 40 along the retraction direction 20.

As the pin wheel 50 meshes with both rows of teeth 60, during one rotation the holding arms 30, 32 are displaced relative to each other over a distance which is twice as large as it would be if only one holding arm 30, 32 were driven with one row of teeth 60. This allows a compact design to be imparted to the retractor 10. As is clear, in particular, from FIG. 1, the holding arms 30, 32 can be of such short dimensions that when the retractor 10 is unspread, they do not project or only to a slight extent over the respective other spreader arm 16, 18.

In addition, it is advantageous that the holding device 28, the pin wheel 50 and the crank 58, in relation to the retraction direction 20, are arranged in a center plane perpendicular to the spreading plane between the spreader arms 16, 18. In particular, the holding device 28, the pin wheel 50 and the crank 58 are arranged midway between the first sections 22. As a result, the holding arms 30, 32 continue to be held on each other via the housing 40 when the spreader arms 16, 18 are spread.

In the event of only slight spreading, the holding arms 30, 32 already no longer project over the respective other spreader arm 16, 18. In addition to the compact design, this construction proves to be particularly user-friendly as the operating surgeon finds it less interfering. Access to the surgical site is obstructed to a lesser extent by the retractor 10 than is the case with generic retractors.

The arrangement of the rows of teeth 60 at least partially within the housing 40 reduces the likelihood that foreign matter such as, in particular, surgical suture material will get caught on the rows of teeth 60. This allows more reliable functioning of the retractor 10.

Moreover, the retractor 10 shows only low wear between components rubbing against one another. The housing 40, on the one hand, and the pin wheel 50, on the other hand, are manufactured or treated so as to reduce wear, for example, by surface or heat treatment such as, for example, nitriding, surface layer hardening, boriding, case hardening or the like. A specified difference in hardness of, for example, at least approximately 25% between the two friction partners is possible. To reduce the friction, the materials can be adapted to one another, for example, as a combination of materials consisting of ceramic material and metal or of plastic material and metal.

Furthermore, slide bearings and/or ball bearings are possible for reducing the friction between the pin wheel 50 and the housing 40. Corresponding materials and/or surface or heat treatments are also possible for further components, in particular, the interacting pins 52 and rows of teeth 60.

Figure 4:
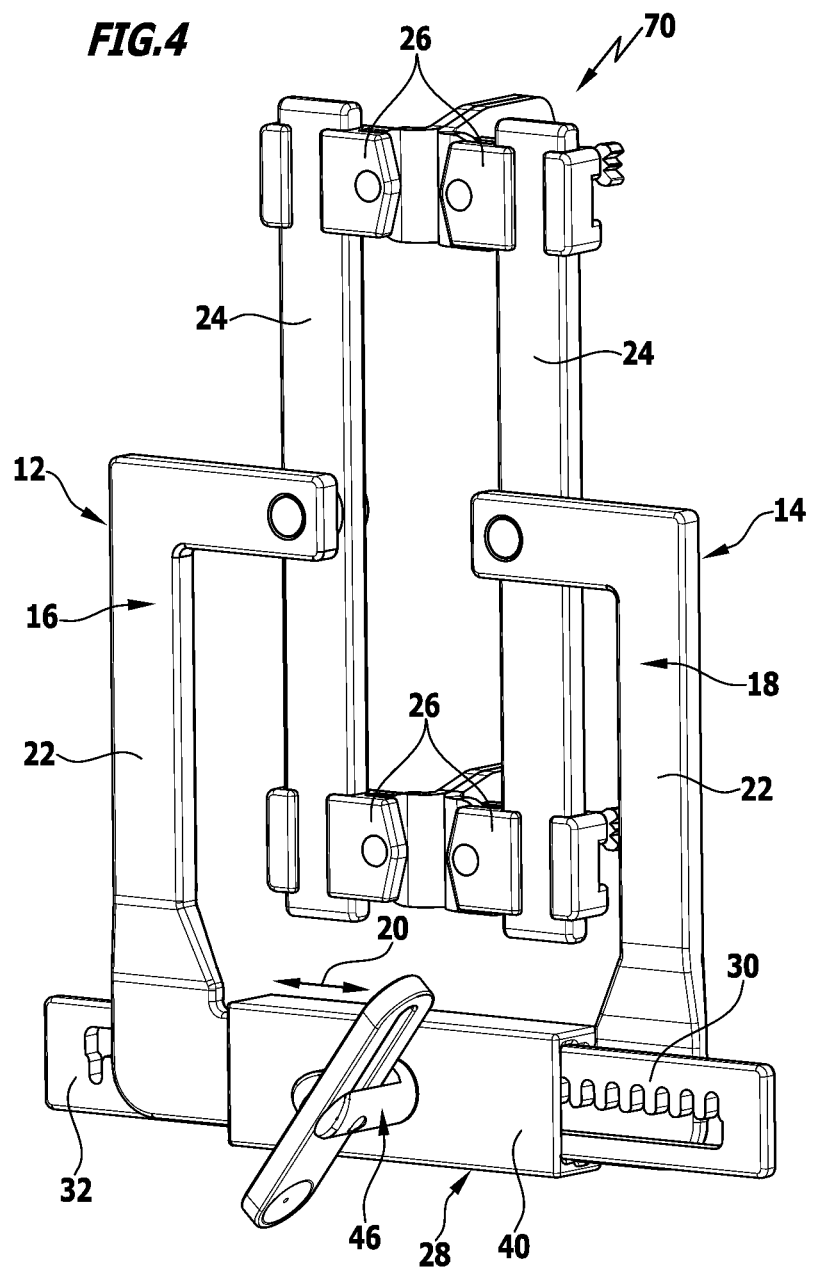
FIG. 4 shows a perspective representation of a second preferred embodiment of a retractor in accordance with the invention.
Figure 5:
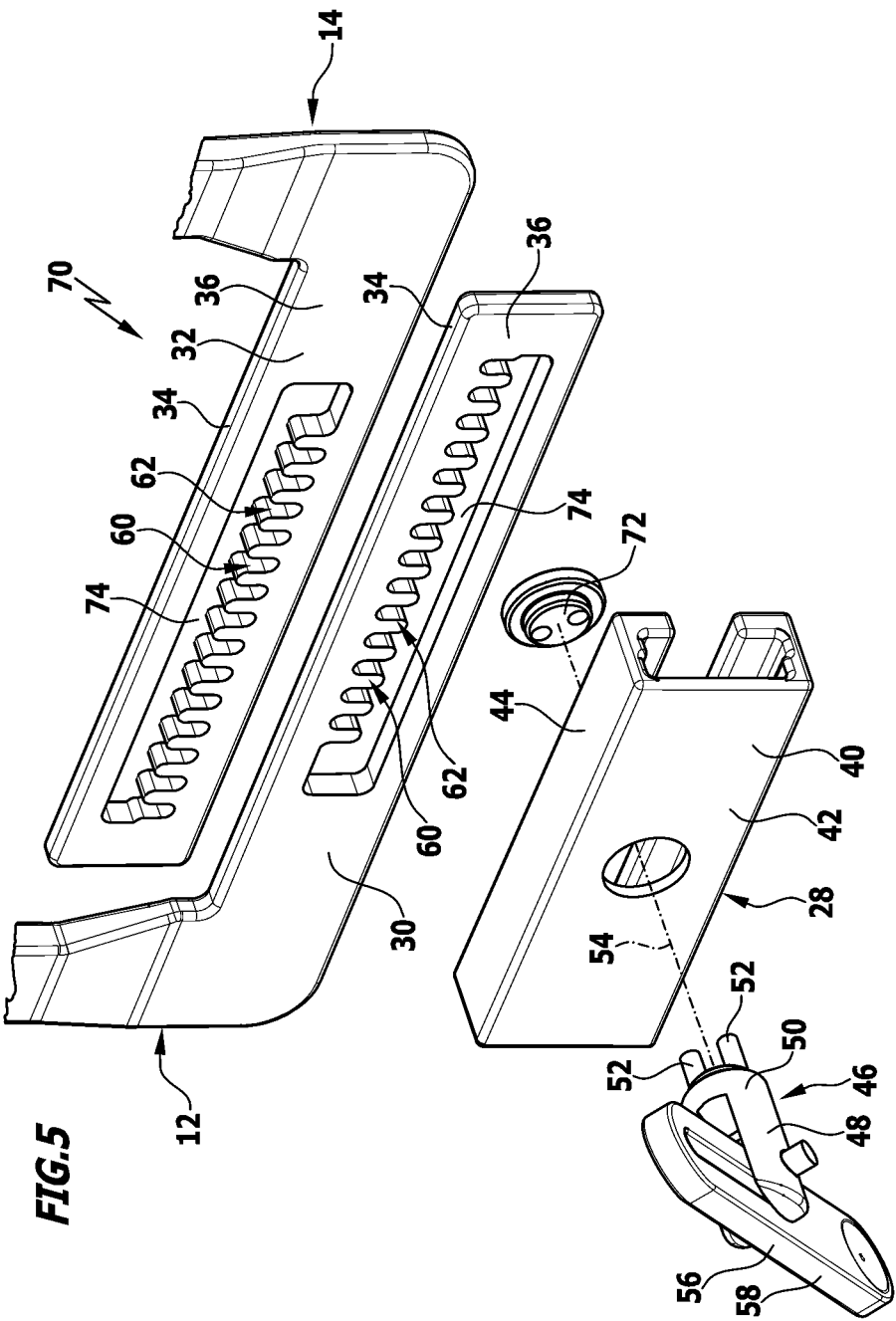
FIG. 5 shows a partial view of the retractor from FIG. 4 in an exploded representation.
Figure 6:
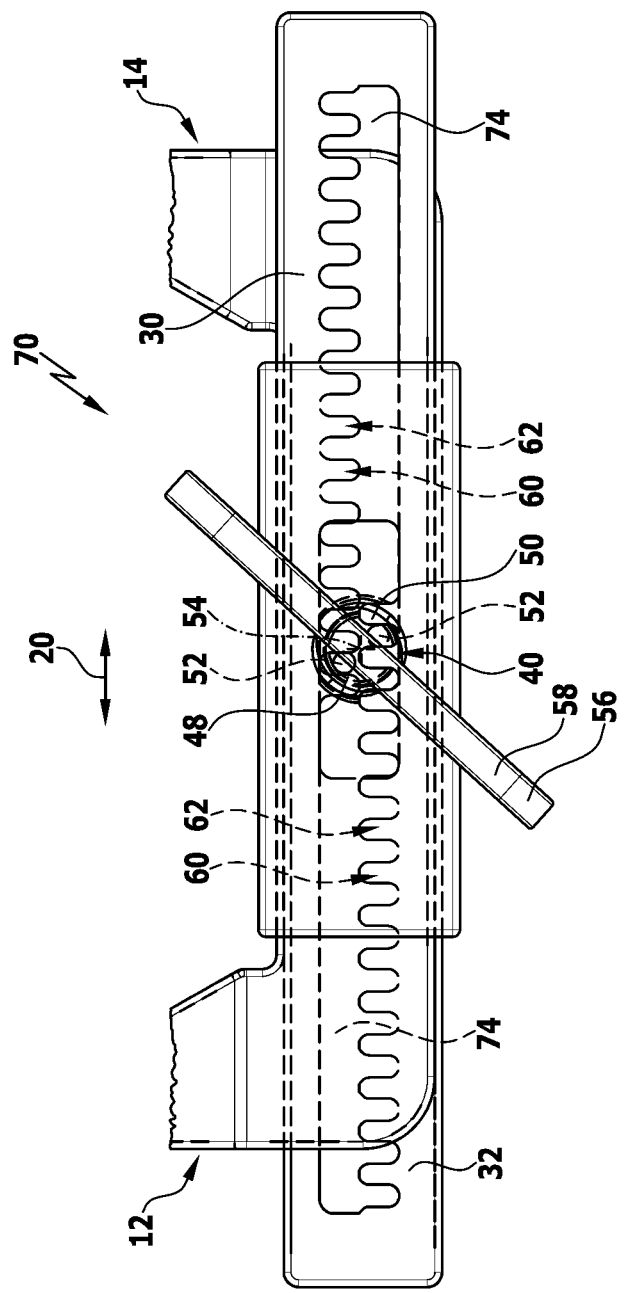
FIG. 6 shows a partial representation of the retractor from FIG. 4 in a plan view.

FIGS. 4 to 6 show a second advantageous embodiment, denoted in its entirety by reference numeral 70, of a retractor in accordance with the invention. The advantages achievable with the retractor 10 can also be achieved with the retractor 70. Therefore, in this respect reference is made to the above explanations in order to avoid repetitions. The same reference numerals are used for features and components of the retractors 10 and 70 which are the same and have the same effect, and the essential differences are described.

In the retractor 70, the holding arms 30, 32 are arranged parallel to each other and lie with surface-to-surface contact via their broad sides 36 against each other so that they can guide each other mutually upon displacement. In addition, both holding arms 30, 32 are guided by the housing 40. In the retractor 70, the housing 40 is not closed in itself in the circumferential direction of the holding arms 30, 32. Opposite a closed broad side 42, the broad side of the housing 40 is open and so the housing 40 has a C-shaped cross section.

This serves to fix the drive element 48 with a fixing element 72 on the housing 40 from the side opposite the closed broad side 42.

The holding arms 30, 32 have elongated holes 74 extending in the longitudinal direction (corresponding to the retraction direction 20). The rows of teeth 60 are arranged at edges of the elongated holes 74, and the teeth of the rows of teeth 60 are formed as projections of the edges of the elongated holes 74.

Each row of teeth extends substantially over a longitudinal edge of an elongated hole 74. The teeth of both rows of teeth 60 face one another and so the pin wheel 50 can simultaneously mesh with the rows of teeth 60 of both holding arms 30, 32 (FIG. 6). The row of teeth 60 on the holding arm 30 faces in a direction facing away from the retaining elements 26, and the row of teeth 60 on the holding arm 32 faces in the direction of the retaining elements 26.

Figure 7:
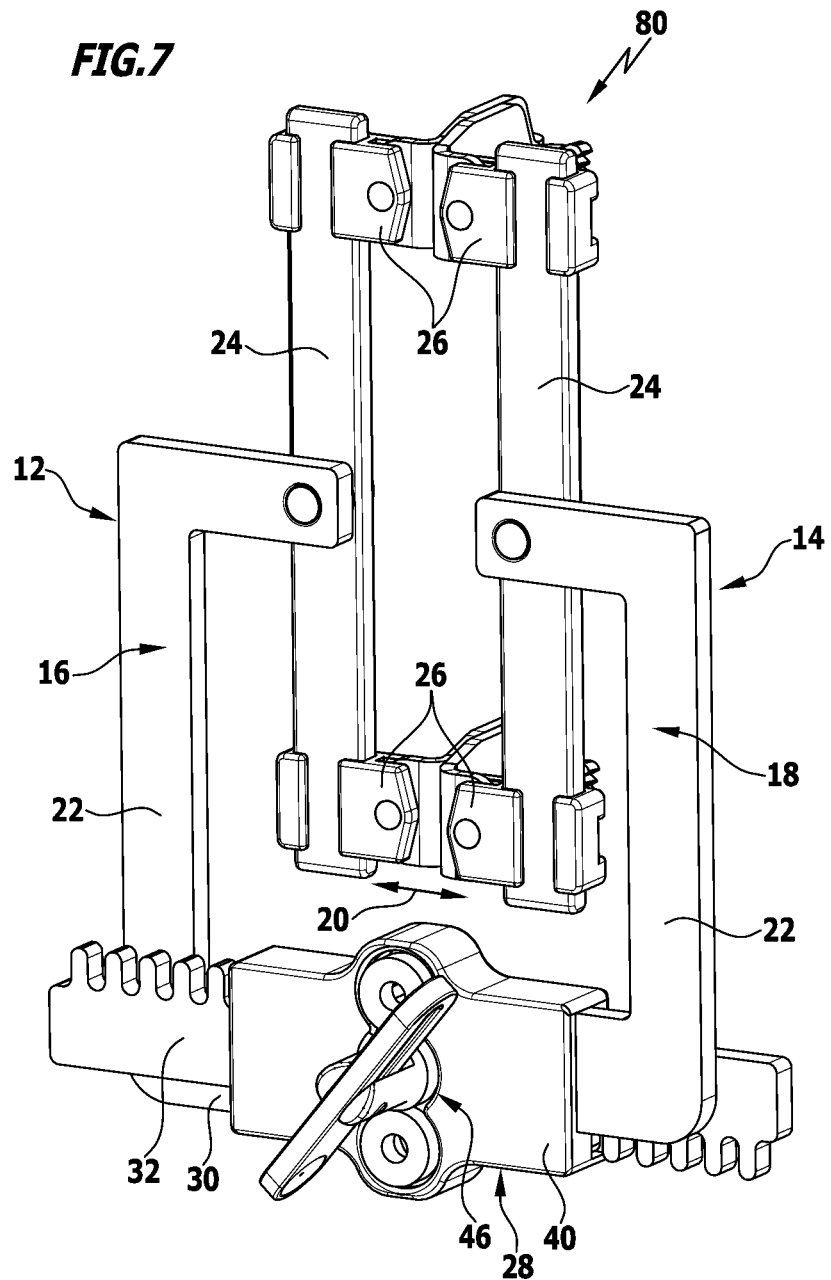
FIG. 7 shows a perspective representation of a third preferred embodiment of a retractor in accordance with the invention.
Figure 8:
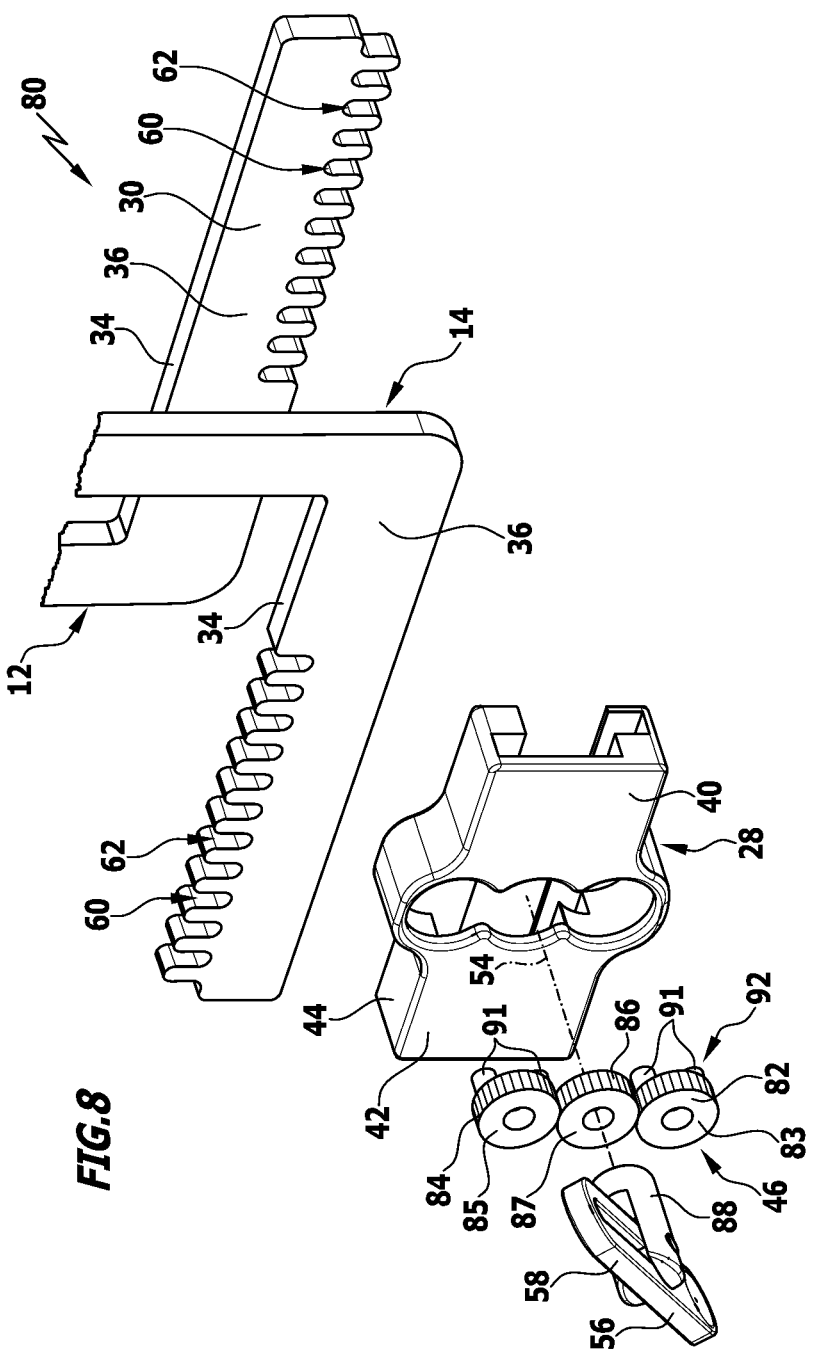
FIG. 8 shows a partial view of the retractor from FIG. 7 in an exploded representation.

FIGS. 7 to 9 show a third advantageous embodiment, denoted in its entirety by reference numeral 80, of a retractor in accordance with the invention. The advantages achievable with the retractor 10 can also be achieved with the retractor 80. Therefore, in this respect reference is made to the above explanations in order to avoid repetitions. The same reference numerals are used for features and components of the retractors 10 and 80 which are the same and have the same effect, and the essential differences are described.

As in the retractor 70, the holding arms 30, 32 in the retractor 80 lie with surface-to-surface contact via broad sides 36 against each other. The rows of teeth 60 are arranged on narrow sides 34, more specifically, in directions facing away from each other. The row of teeth 60 on the holding arm 30 faces away from the retaining elements 26, and the row of teeth 60 on the holding arm 32 faces in the direction towards the retaining elements 26. The rows of teeth 60 extend from the respective free end of a holding arm 30, 32 over approximately 60% of its length. The rows of teeth 60 are formed by cut-outs formed on the narrow sides 34 of the holding arms 30, 32, so that the portions that are not cut out form teeth of the rows of teeth 60.

Like the housing 40 of the retractor 70, the housing 40 is not closed in itself in the circumferential direction of the holding arms 30, 32, but is substantially C-shaped in cross section. At the center of the narrow sides 44, the housing 40 has two convex bulges so that a receiving space is created within the housing 40 for two drive elements 82 and 84 of the drive device 46. The drive elements 82, 84 are configured as gear wheels 83 and 85, respectively.

Arranged between the gear wheels 83, 85 is a further drive element 86 in the form of a gear wheel 87, which simultaneously meshes with both gear wheels 83 and 85 and is rotationally fixedly connected to a drive body 88 of the drive device 46. In the retractor 80 the drive body 88 replaces the pin wheel 50 of the retractor 10, and the crank 58 is secured to it. The drive body 88 and, therefore, the gear wheel 87 are mounted on the housing 40 so as to be rotatable about the axis of rotation 54 perpendicular to the spreading plane. When the gear wheel 87 is rotated, the gear wheels 83 and 85 are simultaneously rotated about axes of rotation 89 and 90, respectively, perpendicular to the spreading plane. All the axes of rotation 54, 89, 90 are arranged in a common plane, namely the center plane of the retractor 80.

Arranged on end faces of the gear wheels 83, 85 are two pins 91, in each case, which are diametrically opposed to each other in relation to the respective axis of rotation 89 and 90 and are in engagement with the rows of teeth 60. When the crank 58 is rotated, each holding arm 30, 32 is thereby rotatingly driven, so that the holding arms 30, 32 can be displaced in opposite directions relative to each other and relative to the housing 40 along the retraction direction 20.

The provision of the gear wheels 83, 85, 87 allows a gearing 92 to be formed with the drive device 46. A rotational speed (number of rotations) of the crank 58 can be geared up or geared down by the gearing 92, in order to adapt the rotational speed of the gear wheels 83, 85 to meet the requirements. In dependence upon the gearing-up or gearing-down, the holding arms 30, 32 can be displaced to a different extent relative to each other with each rotation of the crank 58.

It may be provided that the gear wheels 83, 85 and 87 are exchangeable in order to be able to adapt the gearing-up or gearing-down. A high versatility is thereby imparted to the retractor 80.

The invention claimed is:

1. A surgical retractor configured to spread a severed sternum, comprising:
    a first retaining device and a second retaining device, each of the retaining devices comprising a respective spreader arm with at least one retaining element held thereon,
    a holding device for holding the retaining devices together, and
    a drive device with which a distance of the spreader arms from each other along a retraction direction is alterable for transfer to a spread position,
    each of the retaining devices further comprising a holding arm connected to the respective spreader arm, and
    wherein:
    the holding arms couple with the drive device and are displaceable via the drive device relative to each other and relative to the holding device along a displacement direction,
    the holding arms lie directly against each other and, when displaced, mutually guide each other along the displacement direction,
    the holding arms each having a length defined along the displacement direction, a width transverse to the length, and a thickness transverse to both the length and width, broad sides of each of the holding arms are defined along the width and narrow sides of each of the holding arms are defined along the thickness,
    the holding arms lie via the respective broad sides of the holding arms with surface-to-surface contact against each other, and
    the surface-to-surface contact of the broad sides of the holding arms occurs at least inside a housing formed by the holding device.

2. The surgical retractor in accordance with claim 1, wherein the displacement direction is aligned parallel to the retraction direction.

3. The surgical retractor in accordance with claim 1, wherein at least one of the holding device and the drive device is arranged, in relation to the retraction direction, midway or substantially midway between the spreader arms.

4. The surgical retractor in accordance with claim 1, wherein upon actuation of the drive device, the holding arms are each displaceable over an identical distance relative to the holding device.

5. The surgical retractor in accordance with claim 1, wherein the holding arms comprise rails.

6. The surgical retractor in accordance with claim 1, wherein the holding device comprises the housing which at least partially engages around the holding arms.

7. The surgical retractor in accordance with claim 6, wherein the holding arms engage the housing from opposite sides of the housing and/or extend through the housing.

8. The surgical retractor in accordance with claim 1, wherein the holding device forms a guide for at least one of the holding arms.

9. The surgical retractor in accordance with claim 1, wherein:
    the drive device comprises at least one drive element,
    the holding arms each comprise a drive track extending in the displacement direction, and
    the at least one drive element interacts with the drive tracks.

10. The surgical retractor in accordance with claim 9, wherein:
    the drive tracks are each configured as a row of teeth arranged on the respective holding arm, and
    the at least one drive element is configured as one of a pin wheel or a gear wheel which meshes with the row of teeth of each drive track.

11. The surgical retractor in accordance with claim 9, wherein at least one of the holding arms has an elongated hole aligned along the displacement direction, at an edge of which the drive track is arranged.

12. The surgical retractor in accordance with claim 9, wherein the drive tracks are arranged on sides of the holding arms that face away from each other.

13. The surgical retractor in accordance with claim 9, wherein:
    the drive tracks are arranged on the narrow sides of the holding arms.

14. The surgical retractor in accordance with claim 9, wherein:
    the drive device comprises two drive elements, each of the drive elements interacting with one of the drive tracks of a respective one of the holding arms.

15. The surgical retractor in accordance with claim 14, wherein:
    the drive tracks of the holding arms face each other, and
    each of the two drive elements engages with teeth of the respective drive track.

16. The surgical retractor in accordance with claim 14, wherein:
    the two drive elements are drivable together.

17. The surgical retractor in accordance with claim 16, wherein:
    the drive device comprises a further drive element which is coupled to an actuating element for the drive device, and
    the further drive element meshes with the two drive elements.

18. The surgical retractor in accordance with claim 9, wherein the drive device comprises a gearing with which a rotational speed of the at least one drive element is alterable.

19. The surgical retractor in accordance with claim 18, wherein:
    the holding device comprises the housing, and
    the gearing is located in the housing.

* * * * *